(12) United States Patent
McMillan

(10) Patent No.: US 8,137,053 B2
(45) Date of Patent: Mar. 20, 2012

(54) ASSEMBLY HAVING FIRST AND SECOND MEMBERS DISTINGUISHABLE BY RESPECTIVE FIRST AND SECOND COMPOSITIONS EACH INCLUDING ONE OR MORE ISOTOPES OF A SAME ELEMENT

(75) Inventor: Alison Jane McMillan, Staffordshire (GB)

(73) Assignee: Rolls-Royce, PLC (GB)

( * ) Notice: Subject to any disclaimer, the term of this patent is extended or adjusted under 35 U.S.C. 154(b) by 798 days.

(21) Appl. No.: 12/235,729

(22) Filed: Sep. 23, 2008

(65) Prior Publication Data

US 2009/0104030 A1   Apr. 23, 2009

(30) Foreign Application Priority Data

Oct. 19, 2007   (GB) .................................. 0720452.2

(51) Int. Cl.
*G01M 15/00* (2006.01)
(52) U.S. Cl. ............ 415/9; 415/118; 416/61; 73/112.01
(58) Field of Classification Search ................ 73/112.01
See application file for complete search history.

(56) References Cited

U.S. PATENT DOCUMENTS

| 3,959,069 | A | 5/1976 | McCormick |
| 4,582,671 | A | 4/1986 | Rindo |
| 4,715,988 | A | 12/1987 | Colin |
| 2005/0054914 | A1 | 3/2005 | Duerk et al. |
| 2005/0276742 | A1* | 12/2005 | Fan et al. ................... 423/447.1 |

FOREIGN PATENT DOCUMENTS

| EP | 1154440 A1 | 11/2001 |
| EP | 1324257 A1 | 7/2003 |
| GB | 2208060 A | 2/1989 |

OTHER PUBLICATIONS

Norris, G: "Trent 1000 ready to fly following blade-off test" Flight International (Online), Aug. 29, 2007, XP002513481, Retrieved from the internet.

* cited by examiner

*Primary Examiner* — Stephen W Smoot
(74) *Attorney, Agent, or Firm* — McCormick, Paulding & Huber LLP

(57) ABSTRACT

An assembly includes a first member and a second member, the first member including a first material composition and the second member including a second material composition. The first and second material compositions each include one or more isotopes of the same element, which are arranged to permit distinguishing between the first and second members or 0 parts thereof.

12 Claims, 1 Drawing Sheet

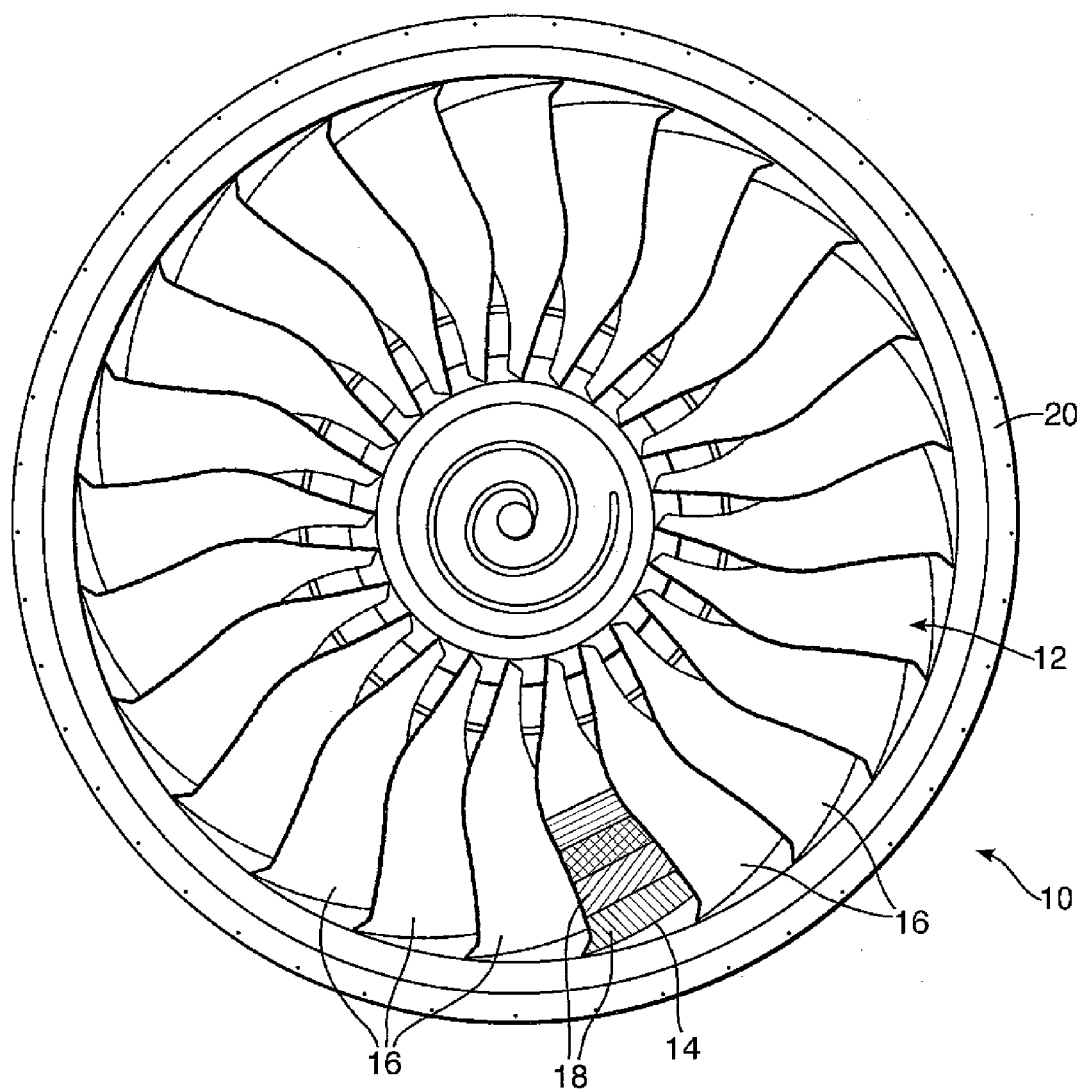

ASSEMBLY HAVING FIRST AND SECOND MEMBERS DISTINGUISHABLE BY RESPECTIVE FIRST AND SECOND COMPOSITIONS EACH INCLUDING ONE OR MORE ISOTOPES OF A SAME ELEMENT

CROSS REFERENCE TO RELATED APPLICATION

This application is entitled to the benefit of British Patent Application No. GB 0720452.2, filed on Oct. 19, 2007.

FIELD OF THE INVENTION

The present invention relates to assemblies, particularly but not exclusively assemblies such as gas turbine engines or parts thereof which are subjected to explosive or highly dynamic/energetic testing.

BACKGROUND OF THE INVENTION

Assemblies such as gas turbine engines are subjected to rigorous testing. For example, gas turbine engines, which include fan blade assemblies are subjected to "fan blade off" tests in which a fan blade is deliberately released during operation to determine the effect of the loss of a fan blade on the mechanical integrity of the engine systems. Typically, the fan blade is released by "explosive" means to separate a portion of the blade from the assembly. In such tests, the explosive serves to initiate a crack across the blade and the momentum of the blade propels the blade to the casing. The separated blade results in damage to other fan blades and the casing of the engine around the fan blade assembly, and other components downstream of the fan, such as outlet guide vane structures.

Conventionally, the release blade is painted with multiple colors, so that after the test the release blade pieces can be identified and distinguished from other pieces originally from other blades and from the casing. The size, shape and location of the fragments of the release blade, other blades and casing provide information as to the effect of the failure of a blade in operation as well as to confirm the accuracy of predictions. However, the paint can become separated from the release blade fragments during the test, making analysis of the failure effects difficult and uncertain.

SUMMARY OF THE INVENTION

According to a first aspect of the present invention, there is provided an assembly, the assembly including a first member and a second member, the first member including a first material composition, the second member including a second material composition, the first and second material compositions each including one or more isotopes of the same element which are arranged to permit distinguishing between the first and second members or parts thereof.

Possibly, the first material composition includes the one or more isotopes in different proportions to the second material composition. Possibly, the proportions are sufficiently different as to be detectable by analysis. The analysis may include spectrographic analysis and/or analysis by nuclear magnetic resonance.

Possibly, the first member and the second member are substantially identical in size and shape. Possibly the first member and the second member have substantially the same mass.

Possibly, one or more of the isotopes is a naturally occurring stable isotope. Alternatively or additionally, one or more of the isotopes may be a radioactive isotope.

Possibly, the assembly includes a plurality of members, each of which is formed of a different composition, each of which may include one or more isotopes of the same element and which are arranged to permit distinguishing between each of the members or the parts thereof.

Possibly, at least one of the compositions comprises a naturally occurring composition and may comprise a plurality of different naturally occurring compositions. Optimally, more than one of the compositions comprise one or more different naturally occurring compositions. Possibly, the different naturally occurring compositions are sourced from different natural sources.

Possibly, the element is one selected from a group consisting of the elements titanium, iron, aluminium, nickel, vanadium, cobalt, carbon, nitrogen, hafnium, magnesium, chromium and copper. Possibly, the element is titanium.

Possibly, in use at least part of the first member is separated from the assembly. Possibly, the assembly includes a plurality of second members. Possibly, the assembly includes another member or plurality of members, the or each of which comprises a different material composition to the first and second material composition, the different material composition or compositions including one or more isotopes of the same element. Possibly, each of the different material compositions is different.

Possibly, each of the compositions is arranged to have substantially the same density. Possibly, the proportion of the isotope in each composition is relatively small. Possibly, the proportion of the isotope in each composition is less than 5%.

Possibly, the assembly is part of an aircraft, and may be a gas turbine engine or a part thereof. Possibly the assembly is a fan blade assembly, and the members may be fan blades.

According to a second aspect of the present invention, there is provided a method of identifying the members of an assembly, the method including the step of providing an assembly including a first member and a second member, the first member including a first material composition, the second member including a second material composition, the first and second material compositions each including one or more isotopes of the same element which are arranged to permit distinguishing between the first and second members or parts thereof.

Possibly, the assembly includes any of the features described above in the preceding statements.

According to a third aspect of the present invention, there is provided a method of testing an assembly, the method including the step of providing an assembly including a first member and a second member, the first member including a first material composition, the second member including a second material composition, the first and second material compositions each including one or more isotopes of the same element which are arranged to permit distinguishing between the first and second members or parts thereof, the method including a step in which one of the members is separated from the assembly.

Possibly, the step of separation is explosive. Possibly, the step of separation is initiated by a small controlled explosion.

Possibly, the assembly includes any of the features described above in the said preceding statements.

BRIEF DESCRIPTION OF THE DRAWING

FIG. 1 is a simplified front view of part of a gas turbine engine.

DETAILED DESCRIPTION OF THE PREFERRED EMBODIMENTS

FIG. 1 shows an assembly in the form of a gas turbine engine 10, the gas turbine engine 10 including a fan blade assembly 12. The fan blade assembly 12 includes a first member in the form of a first fan blade 14 and a plurality of second members in the form of second fan blades 16 (only a few of which are labelled).

The first fan blade 14 is marked with a plurality of painted marker bands 18 of different colors, indicated in FIG. 1 by different hatching styles.

Conventionally, the first and second fan blades 14, 16 are substantially identical, the first fan blade 14 only being differentiated from the second fan blade 16 by the marker bands 18. During a fan blade off test, the first fan blade 14 is explosively released from the fan blade assembly 12 during operation of the gas turbine engine 10, the explosive separation resulting in the break up of the first fan blade 14 and damage to the second fan blades 16 and the engine casing 20.

In a fan blade assembly 12 of the present invention, the first fan blade 14 is formed of a first material composition and the second fan blades 16 are formed of a second material composition, the first and second material compositions each including one or more isotopes of the same element, which are arranged to permit distinguishing between the first and second blades 14, 16 or parts thereof.

TABLE 1

Example 1: Titanium isotopic compositions

| | | Composition 1 | | Composition 2 | |
|---|---|---|---|---|---|
| Isotope | Isotope atomic mass g/mol | Proportions of isotopes % | Mass of each isotope g/mol | Proportions of isotopes % | Mass of each Isotope g/mol |
| $^{46}$Ti | 46 | 100% | 46.00 | 0% | 0 |
| $^{47}$Ti | 47 | 0% | 0.00 | 0% | 0 |
| $^{48}$Ti | 48 | 0% | 0.00 | 0% | 0 |
| $^{49}$Ti | 49 | 0% | 0.00 | 0% | 0 |
| $^{50}$Ti | 50 | 0% | 0.00 | 100% | 50 |
| Composition totals | | 100% | 46.00 | 100% | 50.00 |

TABLE 2

Example 2: Titanium isotopic compositions

| | | Composition 3 | | Composition 4 | |
|---|---|---|---|---|---|
| Isotope | Isotope atomic mass g/mol | Proportions of isotopes % | Mass of each isotope g/mol | Proportions of isotopes % | Mass of each Isotope g/mol |
| $^{46}$Ti | 46 | 8.25% | 3.80 | 52% | 23.92 |
| $^{47}$Ti | 47 | 7.44% | 3.50 | 0% | 0 |
| $^{48}$Ti | 48 | 73.72% | 35.39 | 0% | 0 |
| $^{49}$Ti | 49 | 5.41% | 2.65 | 0% | 0 |
| $^{50}$Ti | 50 | 5.18% | 2.59 | 48% | 24 |
| Composition totals | | 100% | 47.92 | 100% | 47.92 |

Tables 1 and 2 shows examples of differing titanium compositions.

In a first example, referring to Table 1, the first fan blade 14 could be formed of a first material composition including composition 1, composition 1 comprising 100% titanium isotope $^{46}$Ti, and the second fan blades 16 could be formed of a second material composition including composition 2, which comprises 100% titanium isotope $^{50}$Ti. Other parts of the engine such as the casing 20 could also be formed of the second material composition.

Following testing, pieces of material could be analysed for example by spectrographic analysis or by nuclear magnetic resonance to determine the isotopic composition of each piece, which would permit distinguishing between parts derived from the first fan blade 14 and the second fan blades 16 or the engine casing 20.

One of the advantages of the present invention is that the chemical and mechanical characteristics of the fan blades 14, 16 are not substantially altered by the different isotopic compositions. However, there is a difference in the atomic mass of each isotope as is illustrated in Table 1, so that composition 1 has a mass of 46 g/mol and composition 2 has a mass of 50 g/mol. The difference in mass of the compositions will lead to a difference in mass of the fan blades 14, 16, which although relatively slight, may have an effect upon the rotational characteristics of the fan blade assembly 12 and also of the accuracy of the test.

In another example, referring to Table 2, the first fan blade 14 could be formed of a first composition comprising composition 3, which as shown in Table 2 comprises differing proportions of the five naturally occurring isotopes of titanium. The second fan blades 16 could be formed of a second material composition comprising composition 4 including 52% titanium isotope $^{46}$Ti and 48% titanium isotope $^{50}$Ti. In this example, the total mass and therefore the density of each composition is the same, 47.92 g/mol, so that the first fan blade 14 will be substantially identical in weight, shape, and size to the second fan blade 16, so that there is no effect upon the rotational characteristics of the engine 10, and the test simulates real life operation accurately.

There is thus provided an assembly in which different members can be distinguished and identified after explosive testing by virtue of the different isotopic compositions of the members.

Various other modifications could be made without departing from the scope of the invention. The examples described above and shown in Tables 1 and 2 are, for the purposes of illustration, relatively extreme in the differences between the isotopic compositions. However, analysis methods available such as spectroscopy and nuclear magnetic resonance permit relatively small differences in isotopic compositions to be identified. The differences in isotopic compositions only need to be such that the differences are detectable by suitable analysis methods. The differences could be sufficiently small so that the difference in mass between components of different isotopic compositions could be within normal tolerance levels.

Composition 3, in fact, shows the average abundance of different isotopes within titanium. However, these average proportions could vary between naturally occurring sources, and it could therefore be possible to carry out the invention by forming different fan blades from compositions of titanium from different sources, which are naturally of different isotopic composition.

In a further example, a large number of different isotopic compositions could be formed by forming fan blades of naturally occurring titanium compositions from a number of different sources in differing proportions. In one example, each fan blade of a fan blade assembly could be formed of a different isotopic composition by suitable mixture of titanium compositions from different sources.

The fan blades could be formed of alloys including titanium, or could be formed solely of titanium. The isotopic compositions could form only part of the fan blades. The isotopic compositions could form only a relatively small proportion of the alloy. For example, the isotopic compositions could form less than 5% w/w of the alloy.

In another example, a single isotope titanium could be mixed with a standard mixed isotope titanium to provide different isotopic compositions.

In another example, the second fan blade 16 following the first fan blade 14 could be formed of a different isotopic composition to the other second fan blades 16, since this is typically the blade most damaged by release of the first fan blade 14. Alternatively each of the second fan blades 16 could be formed of a different isotopic composition to each other and to the first fan blade 14.

TABLE 3

Iron isotopic composition

| | | Average abundance | |
|---|---|---|---|
| Isotope | Isotope atomic Mass g/mol | Proportions of isotopes % | Mass of each isotope g/mol |
| $^{54}Fe$ | 54 | 5.85% | 3.16 |
| $^{56}Fe$ | 56 | 91.75% | 51.38 |
| $^{57}Fe$ | 57 | 2.12% | 1.21 |
| $^{58}Fe$ | 58 | 0.28% | 0.16 |
| Composition total | | 100% | 55.91 |

TABLE 4

Nickel isotopic composition

| | | Average abundance | |
|---|---|---|---|
| Isotope | Isotope atomic Mass g/mol | Proportions of isotopes % | Mass of each isotope g/mol |
| $^{58}Ni$ | 58 | 68.08% | 39.49 |
| $^{60}Ni$ | 60 | 26.22% | 15.73 |
| $^{61}Ni$ | 61 | 1.14% | 0.70 |
| $^{62}Ni$ | 62 | 3.63% | 2.25 |
| $^{64}Ni$ | 64 | 0.93% | 0.60 |
| Composition total | | 100% | 58.76 |

Other elements having different isotopic compositions could be used instead of, or as well as, titanium. For example, compositions including nickel and iron are common. Table 3 shows the average abundance of iron isotopes, and Table 4 shows the average abundance of nickel isotopes. In the same way as described above, the isotopic composition of these elements could be varied for different components to permit distinguishing and identification of parts after testing.

Another metal commonly included in aerospace alloys is aluminium. However, aluminium is normally found with only one naturally occurring stable isotope. However, it could be possible to form a radioactive isotope, which could be used to permit different isotopic compositions of parts. A radioactive isotope could also assist in the detection process, since it would permit the use of radioactive detection apparatus, which could differentiate between radioactive and non radioactive parts. The radioactive isotope could have a half life which is sufficiently long so that there is no significant build up of decay products which could compromise the material properties of the component.

Any suitable radioactive isotope of any suitable element could be used.

In another example an alloy comprising predominantly of one element such as aluminium or titanium could also include a relatively small proportion of an isotopic composition of another element, which isotopic composition could be varied between the different members of an assembly. For example, in a composition comprising predominantly of titanium, different components could have different isotopic compositions of vanadium, which occurs naturally as two isotopes, $^{50}V$ and $^{51}V$, or of aluminium as discussed above. One example of such a composition is "Titanium 6/4" which is a composition used for fan blades, and includes 6% aluminium and 4% vanadium. Thus, instead of varying the isotopes of titanium, those of vanadium or aluminium could be varied instead.

Any other suitable elements, which may not necessarily be metals could be used, such as cobalt, carbon, nitrogen or hafnium. For example, components could be formed wholly or partially of carbon fibre. Carbon naturally occurs as two stable isotopes $^{12}C$ and $^{13}C$ and thus components of or including carbon fibre composite, or having a composition including carbon, could be formed of different isotopic compositions.

Different, naturally occurring isotopic compositions could be derived from any suitable source. For example, it may be possible to derive different isotopic compositions from extra terrestrial material, such as material derived from meteorites.

The invention could be suitable for any assembly in which it is desired to identify parts, which include or are formed of the same element, but require different parts to be distinguished after separation. For example, an airframe of an aeroplane could be formed in sections, each section being formed of an isotopically different composition, permitting easier identification of the parts of the airframe in the event of a crash. Any suitable parts of an assembly could be formed of materials of different isotopic composition.

What is claimed is:

1. An assembly comprising:
a first member including a first material composition,
a second member including a second material composition,
the first and second material compositions each including one or more isotopes of the same element which are arranged to permit distinguishing between the first and second members or parts thereof, wherein the assembly is part of an aircraft.

2. An assembly according to claim 1, in which the first material composition further comprises one or more isotopes in different proportions to the second material composition.

3. An assembly according to claim 1, in which the element is selected from a group consisting of the elements titanium, iron, aluminium, nickel, vanadium, cobalt, carbon, nitrogen, hafnium, magnesium, chromium and copper.

4. An assembly according to claim 1, in which in use at least part of the first member is separated from the assembly.

5. An assembly according to claim 1, in which the assembly includes a plurality of second members.

6. An assembly according to claim 1, in which the assembly includes another member or plurality of members, each of which comprises a different material composition to the first and second material composition, the different material composition or compositions including one or more isotopes of the same element.

7. An assembly according to claim 1, in which each of the compositions is arranged to have substantially the same density.

8. An assembly according to claim 1, in which the proportion of the isotope in each composition is less than 5%.

9. A gas turbine engine comprising:
a first member including a first material composition,
a second member including a second material composition,
the first and second material compositions each including one or more isotopes of the same element which are arranged to permit distinguishing between the first and second members or parts thereof.

10. A fan blade assembly comprising:
a first member including a first material composition,
a second member including a second material composition,
the first and second material compositions each including one or more isotopes of the same element which are arranged to permit distinguishing between the first and second members or parts thereof, and the members are fan blades.

11. A method of testing a rotating fan blade assembly, the assembly including a first member and a second member, the first member including a first material composition, the second member including a second material composition, the first and second material compositions each including one or more isotopes of the same element which are arranged to permit distinguishing between the first and second members or parts thereof, the method including a step in which one of the members is separated from the assembly during rotation, the method including a subsequent step in which the assembly is inspected to identify one or more locations of the first member and of the second member.

12. A method of testing an assembly according to claim 11, in which the step of separation is explosive or initiated by explosion.

* * * * *